United States Patent
Kesling

[11] Patent Number: 5,813,853
[45] Date of Patent: Sep. 29, 1998

[54] TORQUE/ROTATION BASE FOR ORTHODONTIC ATTACHMENT AND METHOD OF MAKING SAME

[76] Inventor: Peter C. Kesling, 611 W. 250 South, LaPorte, Ind. 46350

[21] Appl. No.: 624,716

[22] Filed: Mar. 26, 1996

[51] Int. Cl.⁶ .................................................. A61C 7/00
[52] U.S. Cl. ........................................ 433/9; 433/8
[58] Field of Search ............................ 433/8, 9, 10, 11, 433/13, 16

[56] References Cited

U.S. PATENT DOCUMENTS

| | | |
|---|---|---|
| 3,477,128 | 11/1969 | Andrews . |
| 3,660,900 | 5/1972 | Andrews ........................ 433/16 |
| 3,881,252 | 5/1975 | Andrews . |
| 4,068,379 | 1/1978 | Miller et al. . |
| 4,597,739 | 7/1986 | Rosenberg ........................ 433/9 |
| 4,659,309 | 4/1987 | Merkel ........................ 433/9 |
| 5,722,826 | 3/1998 | Tuneberg et al. ........................ 433/9 |

OTHER PUBLICATIONS

TP, Laboratories, Inc., Products Catalogue, 1974, p. 76.
TP, Laboratories, Inc., Catalogue/907, 1984, p. 6.
"TIP Edge Today," TP Orthodontics, Inc., Fall, 1993, p. 2.

*Primary Examiner*—Ralph A. Lewis
*Attorney, Agent, or Firm*—Lloyd L. Zickert

[57] ABSTRACT

A base for an orthodontic attachment such as a bracket for incorporating torque or rotation in the bracket, which includes a body of wedge shape that may be suitably oriented on and attached to the backside of an orthodontic attachment for selectively incorporating torque or rotation into the bracket. The base may be stamped from a strip of material having a varying thickness such that the base will have a wedge shaped cross section.

8 Claims, 2 Drawing Sheets

TORQUE/ROTATION BASE FOR ORTHODONTIC ATTACHMENT AND METHOD OF MAKING SAME

DESCRIPTION

This invention relates in general to a wedge-shaped base for attachment to the backside of an orthodontic attachment such as a bracket so that depending upon the orientation with respect to the attachment torque or rotation will be incorporated in the attachment, and more particularly to a wedge-shaped base having on one side a surface that enhances its bondability to a tooth. This invention also relates to the method of making a wedge-shaped base from a strip of material having a varying thickness by stamping or punching the base from the strip.

BACKGROUND OF THE INVENTION

It is well known that brackets are made with special archwire slots for coacting with straight archwires and counteracting undesired rotations of canines and premolars during retraction and/or space closure. Similarly, brackets have been propped away from the teeth or the bracket bases on one side to hold anterior teeth in positions of overcorrection or torque. It is also common to incorporate torque into brackets for obtaining a predetermined inclination of a tooth.

Heretofore, torque or rotation have been incorporated into an edgewise orthodontic attachment such as a bracket utilizing various manufacturing systems. For example, the archwire slot may be cut to incorporate torque or rotation into a bracket. Another system includes casting the attaching side of the bracket wherein it is integrally formed with the bracket body and tie wings so as to incorporate torque. When incorporated into the base, such as in U.S. Pat. No. 3,477,128 patent, the bracket base is fully integral with the other parts of the bracket. Incorporating torque and/or rotation into the bracket archwire slot requires casting or milling of the slot in accordance with the desired torque and/or rotation for a specific bracket. It has also been known to build the torque into the bracket body as taught in U.S. Pat. No. 4,659,309. Thus, torque may be built into orthodontic brackets by cutting or casting the archwire slot at an angle to the base or by casting or milling the base of the bracket at a predetermined angle.

Moreover, it has been well known to bend archwires to coact with standard brackets to torque and/or rotate teeth.

SUMMARY OF THE INVENTION

The orthodontic attachment of the present invention overcomes the individual manufacture of orthodontic appliances such as brackets with torque or rotation, or the custom cutting or casting of the archwire slot to provide torque or rotation, or the bending of archwires with standard brackets, by mounting a wedge-shaped base to the backside of a standard bracket having zero torque and zero rotation to incorporate either torque or rotation into the bracket. It is then possible to reduce inventories of brackets designated with various values of torque or rotation. Further, the base to be added may be standardized except for defining different degrees of torque or rotation and used either to incorporate torque or rotation into a standard bracket.

A range of wedge angles for the bases could be between 4 and 25 degrees. Moreover, the base would include one face attachable to the backside of a bracket and another face formed to enhance bonding to a tooth or for attachment to a tooth band. It should be appreciated that the base of the present invention could also be attached to either a cast or stamped bracket.

Preferably, the wedge-shaped base will include a base layer of metal such as stainless steel, and a mesh layer of stainless steel of a suitable mesh size for bonding procedures and suitably secured or laminated to the base layer such as by diffusion bonding as disclosed in U.S. Pat. No. 4,068,379. While the wedge-shaped base of the present invention would preferably be symmetrically formed by having different thicknesses at opposite edges in one direction in order to define the base as being wedge-shaped, it could be otherwise shaped for a particular bracket to serve only for incorporating torque or rotation. Where the bracket is to be attached to a band, the base will be wider than the bracket to enable spot-welding to the band.

Further, it should be appreciated the base may be made of plastic, such as when used to be attached to a ceramic or plastic bracket for incorporating torque or rotation. Such a plastic base may be cast, molded or otherwise formed.

Further, the present invention relates to the method of making the wedge-shaped base, wherein a strip of material formed to have a thicker portion along one side is subjected to a stamping or punching operation to form the wedge-shaped bases having opposing edges of varying thicknesses. Preferably, metal strip material used for the formation of the bases would include a face on one side for attachment to the backside of a bracket such as by welding, soldering or brazing to transform a standard metal bracket into one having a desired torque or a desired rotation. The other side of the base would preferably include a mesh layer that is suitably secured to the plate in the formation of the strip material. For example, the material may be made by joining the mesh with the plate as set forth in U.S. Pat. No. 4,068,379, or by any other suitable method. Thereafter, the material may be formed by removal of material from the face opposite the mesh so that it would have a greater thickness in one area than in another area. With respect to plastic bases, a strip of plastic may be extruded or molded to a desired shape or a uniform thickness strip may have material removed from one surface to define the strip with varying thickness.

It is therefore an object of the present invention to provide a new and improved base for attachment to the backside of a standard orthodontic attachment, wherein the base is wedge-shaped and capable of being used to incorporate torque or rotation into the attachment.

A further object of the present invention is in a method to make wedge-shaped bases from a strip of material having a mesh layer secured to a plate layer of varying thickness to enable the stamping or punching therefrom of a wedge-shaped base.

Other objects, features and advantages of the invention will be apparent from the following detailed disclosure, taken in conjunction with the accompanying sheets of drawings, wherein like reference numerals refer to like parts.

DESCRIPTION OF THE INVENTION

The present invention is directed to a unique orthodontic attachment incorporating torque or rotation by mounting a wedge-shaped base to the backside of a standard orthodontic attachment having zero torque and zero rotation. Thus, standard attachments, such as brackets having a horizontally opening archwire slot with zero torque and zero rotation, can be transformed into brackets having a selected torque value or rotation value by attaching wedge-shaped bases according to the invention to the backside of the brackets. The present invention is particularly useful in connection with providing torque or rotation to a stamped bracket that would be more economical to manufacture. Similarly, a cast bracket of one configuration that would have zero rotation and/or zero torque would be easier to make on a mass production basis.

Moreover, it should be appreciated that the incorporation of torque or rotation into a standard bracket may also be accomplished with respect to plastic or ceramic brackets wherein a suitable plastic-formed base that is wedge-shaped can be added to the backside of a standard bracket configuration. While the wedge-shaped bases of the present invention are normally used for purposes of incorporating torque or rotation into an orthodontic bracket, it should be appreciated that they could also be used for incorporating torque or rotation into buccal tubes. Also, the wedge-shaped base of the present invention could be used in connection with any other orthodontic attachment that would normally have zero torque or zero rotation wherein it was desired to incorporate torque or rotation into the attachment.

Figure 1:
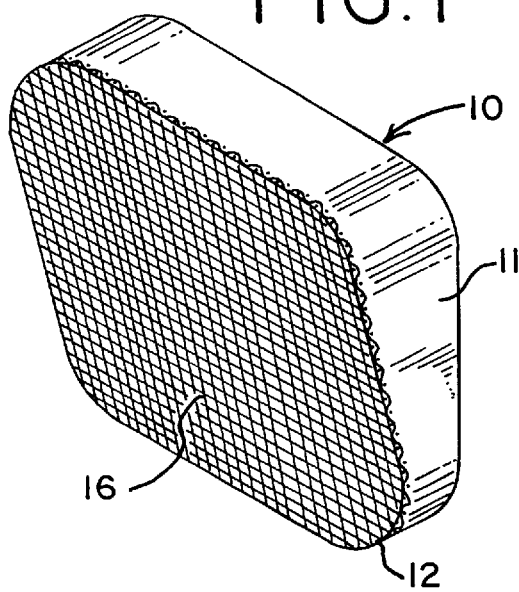
FIG. 1 is a perspective view of the wedge-shaped base in accordance with one embodiment of the invention and showing the tooth-attaching side of the base.
Figure 2:
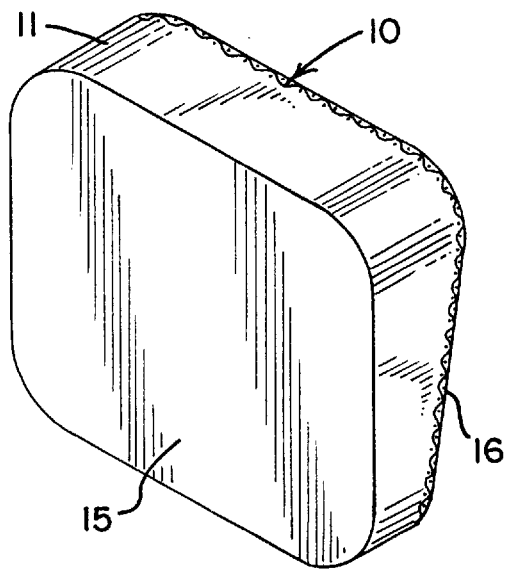
FIG. 2 is a perspective view of the base of FIG. 1 and showing the side of the base attachable to a bracket.

The wedge-shaped base of the invention is shown in FIGS. 1 and 2, and generally designated by the numeral 10, wherein it includes primarily a solid layer 11 and a mesh layer 16. Thus, the mesh layer 16 is suitably secured or laminated to the solid layer 11. It will be appreciated that this particular embodiment would constitute a metal base and preferably of stainless steel wherein the solid layer 11 is of stainless as well as the mesh layer 16. Any other suitable materials may be used. The overall configuration of the wedge-shaped base is preferably rectangular in shape, looking either at the front or back face, although it may be of any other suitable shape for use in securing to the backside of an orthodontic attachment. Further, while the corners of the base are rounded, they may be squared, if desired. Preferably, they are rounded to smooth the corners and reduce the presence of sharp images within the mouth. As particularly seen in FIGS. 1 and 2, the base is wedge-shaped in that the overall base is wider at the upper end than at the lower end, although the orientation of the base relative to an orthodontic attachment will be determined as to whether there is intended to include rotation or torque into the overall combination bracket and base.

With respect to the base 10, the front face may be smooth, as illustrated, and as indicated by the numeral 15, while the rear face can be photoetched or have a mesh configuration, as indicated by the numeral 16. The front face will be adapted to be suitably secured to the backside of an orthodontic attachment, as referred to below, while the back or rear face 16 will be suitably bonded to the surface of a tooth by a suitable bonding material. It is well known that photoetching or a mesh material will provide suitable undercuts and/or indents to enhance the bonding relationship between the mesh and the bonding material, thereby providing an acceptable bond between the appliance and the tooth. Even though the front surface 15 of the base is essentially smooth, it need not be smooth in order to be properly secured to an orthodontic attachment. The thickness of the base varies between two opposing edges in that it then takes on a wedge shape which will, when combined with a bracket having zero rotation and/or zero torque, incorporate into the bracket torque or rotation depending upon the manner in which the base is attached to the bracket.

While the embodiment shown in FIGS. 1 to 2 includes a front face 15 that is substantially flat and a rear face 16 that is substantially flat, it should be appreciated that a curvature may be incorporated into the entire base either between the top and bottom edges or the opposing side edges, depending upon whether the base is to be used to incorporate rotation or torque into an orthodontic attachment. Any suitable forming method may be used to incorporate the curvature.

Further, it should be appreciated that while the exact configuration of the base in FIGS. 1 and 2 would provide a predetermined amount of rotation or torque for a bracket, the shape of the wedge may be adjusted to provide any desired degree of rotation or torque merely by reshaping the wedge-shaped form of the base.

Figure 7:
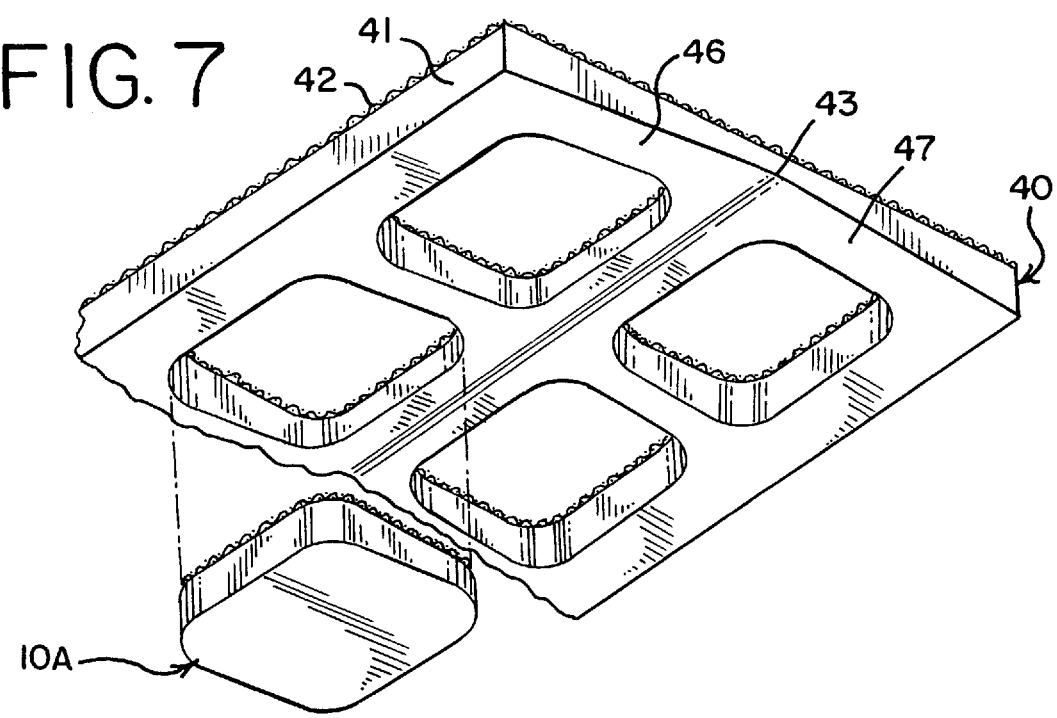
FIG. 7 is a fragmentary perspective view of a strip of material from which wedge-shaped bases are stamped or punched and illustrating the punching of bases.

The base of FIGS. 1 and 2 may easily be made by punching parts from a strip of plate/mesh material that has been formed to define wedge-shaped bases upon the stamping of the parts from the strip. Any suitable punching or stamping equipment may be used to form the parts. A fragmentary strip is illustrated in FIG. 7. This strip illustrates a plurality of punched openings and one punched base to illustrate the manner in which the bases are punched from a strip of material. The strip of material, which is generally indicated by the numeral 40, is initially obtained from a suitable source that is capable of suitably bonding a layer of mesh to a plate to provide the combination plate and mesh. Thereafter, the plate side of the composite material is suitably deformed such as by milling in order to define the material of varying thickness so that when parts are punched therefrom, they will take on the form of a wedge-shaped base. Further, it should be appreciated that while two rows of bases may be punched from a single strip of material, any number may be punched from the material, if desired. If the material of the strip is narrow enough, it can be appreciated that only a single row of bases will be punched from the material.

As particularly seen in FIG. 7, the strip includes a layer of plate 41 and a layer of mesh 42 bonded to the plate on one side thereof. By milling down the plate 41, inclined surfaces 46 and 47 are formed which define toward the center line of the plate portions having varying thickness such that when bases are punched from those portions they will define a wedge-shaped member. Thus, taking a strip of stock which would comprise the plate/mesh composite and varying the thickness of the stock by removing metal from the plate side of the stock prepares the stock for submitting it to a punching or stamping operation in order to punch or stamp out suitably wedge-shaped bases. Thereafter, these bases may be suitably mounted on orthodontic appliances in order to provide rotation or torque.

Figure 3:
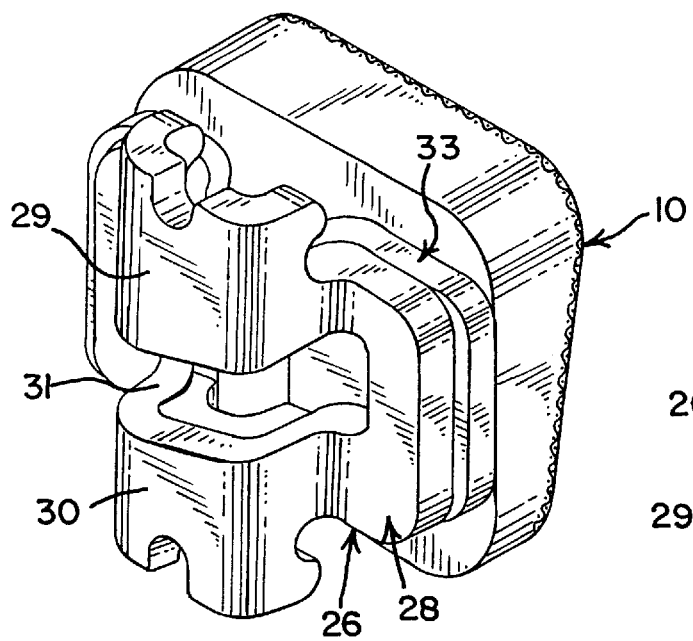
FIG. 3 is a perspective view of a stamped bracket having the base of FIGS. 1 and 2 attached to the backside thereof and incorporating torque.
Figure 4:
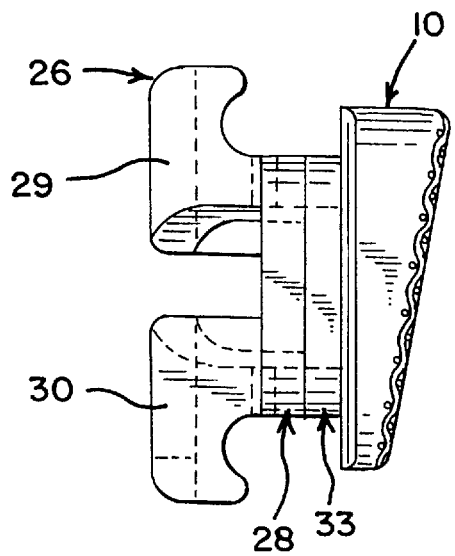
FIG. 4 is an end elevational view or a mesial or distal view of the bracket base combination of FIG. 3.
Figure 5:
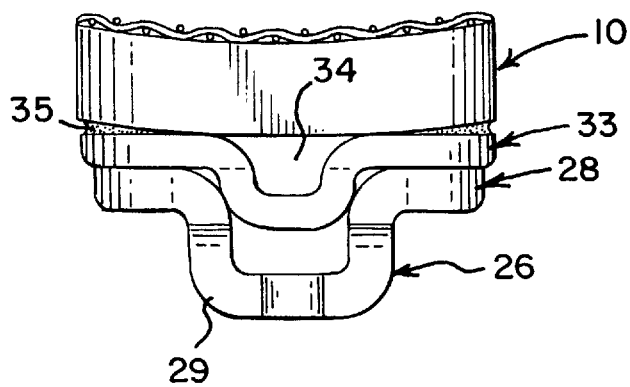
FIG. 5 is a gingival or top plan view of the bracket and base combination of FIG. 3.

As shown in FIGS. 3, 4 and 5, the wedge-shaped base 10 is mounted on a bracket 26 in order to incorporate a torque in the bracket. The base 10 is mounted on a bracket, as shown in FIG. 6, in order to incorporate rotation in the bracket.

The bracket 26 is stamped from sheet material in two parts which are later joined together, which includes a tie wing member 28 for defining opposed tie wings 29, 30 and an archwire slot 31, and a vertical slot or opening member 33 for defining a vertical slot or opening 34 to facilitate the use of auxiliaries. It will be appreciated that the tie wing member and slot member of the bracket 26 may be made from blanks of sheet material that is thereafter suitably formed to give it the shape as shown in the drawings. Thereafter, the two members are joined together as illustrated in piggy-back form and suitably connected such as by brazing or soldering to form the appliance. Finally, it will be appreciated that the appliance thereafter would be tumbled in the usual manner to remove burrs and rough edges from the outer part of the appliance.

Figure 6:
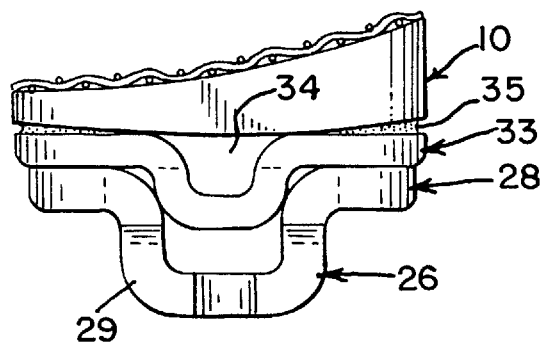
FIG. 6 is a top plan view of the bracket and base oriented to incorporate rotation.

It will now be appreciated that the unique wedge-shaped base 10 of the present invention may be attached to the backside of the appliance by brazing or soldering, as illustrated by the brazing or soldering shown in FIGS. 5 and 6 and indicated by the numeral 35.

As noted in FIGS. 1 and 2, the wedge-shaped base of the invention is essentially rectangular in form or essentially square in form, whereby it is unique in that it can be mounted on the back of a bracket with the thickest edge at the gingival or occlusal side of the bracket to incorporate torque into the bracket, as shown in FIG. 5, or rotated 90 degrees so that the thickest edge is at the mesial or distal side of the bracket in order to incorporate rotation, as illustrated FIG. 6. As already mentioned, although the base as illustrated is essentially square in form, it could be of any other suitable shape and still be used to incorporate either torque or rotation into an appliance. Further, it may be noted that in the embodiment of FIGS. 1, 2 and 3, the base is essentially flat in form, while a curvature is provided to the base in FIGS. 5 and 6 for the purposes of providing better mating relation when being bonded to a tooth. While the wedge-shaped base of the present invention has been illustrated with a single wing bracket, it could also be used with twin brackets or any other type of attachment where it may be desired to incorporate torque or rotation.

The wedge-shaped base of the present invention is inexpensively manufactured from a strip of stock material having a layer of solid material suitably bonded to a layer of mesh material. For example, the mesh material may be diffusion-bonded to the solid layer of material. Thereafter, the layer of solid material may have the smooth side formed so that when bases are punched out of the material, they will take a wedge shape. A suitable machining method may be used to cut down the material at any suitable angle. For example, a milling or grinding operation may be employed which would result in shaping the stock material with a varying thickness so that when a base is stamped therefrom, it will provide a wedge-shaped base. The thickness of the layer of solid material may vary depending on the desired angle of the wedge base, and this layer may be of a suitable stainless steel or other metal compatible with the bracket. Further, the mesh would be of a similar material and of any desired mesh size and wire diameter.

As seen in FIG. 7, a strip of material has been prepared for the stamping operation, which is generally designated by the numeral 40, and includes a layer of solid metal 41 having a layer of mesh material 42 bonded to the one face of the solid layer 41. Preferably, as above noted, these materials are stainless steel, but they could be of any suitable metal. The face of the solid layer 41 is subjected to a grinding operation so that the thickness in the center of the strip at 43 is thinner than the outer edges to define inclined faces 46 and 47. Thus, the thickness varies between the outer edges and the center so that when bases are stamped or punched from the strip, they will have a wedge shape, as illustrated by the single punch 10A. In this regard, bases may be punched from each side of the strip to enhance the economy of making the base. It will be appreciated that depending upon the removal of metal from the smooth side of the stock material, the angle of the base for producing a predetermined torque or rotation may be varied. Further, the stamping or punching operation is preferably performed from the mesh side.

While the base is illustrated as including a mesh layer on the bonding side, it should be appreciated the bonding side may be otherwise formed to define a suitable bonding face. For example, the bonding face may be photoetched. Further, while the base is shown to have substantially the same width as the bracket, it will be understood that where the bracket is to be mounted on a band, the base would be wider to facilitate spot-welding the base to the band, and then the side engaging the band may be substantially smooth.

In view of the foregoing, it may be appreciated that the unique wedge-shaped base of the present invention provides an inexpensive part that may be used with a standard bracket to incorporate torque or rotation into the bracket of any desired value by merely choosing a particular base to put on a standard appliance having zero torque and zero rotation.

It will be understood that modifications and variations may be effected without departing from the scope of the novel concepts of the present invention, but it is understood that this application is to be limited only by the scope of the appended claims.

The invention is hereby claimed as follows:

1. The method of making a substantially rectangular pad for an orthodontic attachment from a strip of plate/mesh material having a thickness varying between two opposing edges, said method comprising the steps of: deforming a strip of plate/mesh material so that it will have a varying thickness, and stamping substantially rectangularly shaped pads therefrom.

2. The method of making a wedge-shaped substantially rectangular base for an orthodontic attachment from a strip of material having opposed faces, said method comprising the steps of: deforming the material strip on one of said faces so that it will have at least one section with a varying thickness, and stamping bases from said section to produce bases having a varying thickness between two opposed edges thereof.

3. The method of claim 2, wherein one of said faces of the material strip includes means enhancing the bonding to a tooth.

4. The method of claim 3, wherein said means includes a layer of mesh.

5. The method of claim 2, wherein the metal strip includes a layer of sheet metal and a layer of metal mesh bonded thereto.

6. The method of claim 2, wherein the strip is plastic.

7. The method of claim 5, wherein the step of stamping is performed from the face having the metal mesh.

8. The method of claim 2, wherein the strip includes two sections of varying thickness and stamping bases from each section produces bases having a varying thickness between two opposed edges.

\* \* \* \* \*